(12) United States Patent
Merz et al.

(10) Patent No.: US 9,632,049 B2
(45) Date of Patent: Apr. 25, 2017

(54) INTEGRATED CIRCUIT AND MANUFACTURING METHOD THEREFOR

(75) Inventors: Matthias Merz, Leuven (BE); Roel Daamen, Herkenbosch (NL); Aurelie Humbert, Brussels (FR); Youri Victorovitch Ponomarev, Leuven (BE)

(73) Assignee: AMS INTERNATIONAL AG, Rapperswil-Jona (CH)

( * ) Notice: Subject to any disclaimer, the term of this patent is extended or adjusted under 35 U.S.C. 154(b) by 1818 days.

(21) Appl. No.: 12/962,460

(22) Filed: Dec. 7, 2010

(65) Prior Publication Data

US 2011/0296912 A1   Dec. 8, 2011

(30) Foreign Application Priority Data

Dec. 7, 2009   (EP) ................................... 09178227

(51) Int. Cl.
| | | |
|---|---|---|
| G08B 21/00 | (2006.01) |
| G01R 27/26 | (2006.01) |
| G01R 27/08 | (2006.01) |
| G01N 27/12 | (2006.01) |
| G01M 3/04 | (2006.01) |
| G01N 27/06 | (2006.01) |

(52) U.S. Cl.
CPC ......... G01N 27/121 (2013.01); G01M 3/045 (2013.01); G01N 27/06 (2013.01)

(58) Field of Classification Search
CPC ............... A61F 13/42; A61F 2013/424; B32B 17/10174; G01F 23/242; G01F 23/243; G01F 23/241; G01F 23/248; G01F 23/266; G01F 23/268; G01N 27/048; G01N 27/121; G01N 27/223; H05K 1/0298; H05K 3/0058
See application file for complete search history.

(56) References Cited

U.S. PATENT DOCUMENTS 3,200,388 A * 8/1965 Uhlig .......................... 340/604
3,523,244 A * 8/1970 Chleck et al. ............ 324/689
(Continued)

FOREIGN PATENT DOCUMENTS

| | | |
|---|---|---|
| DE | 10 2006 050107 A1 | 1/2008 |
| JP | 55 147343 A | 11/1980 |
| WO | 2009/115313 A1 | 9/2009 |

OTHER PUBLICATIONS

A Table for the Solubility of Salts in Water, accessed Aug. 25, 2014.*
(Continued)

*Primary Examiner* — Emily C Terrell
(74) *Attorney, Agent, or Firm* — McDermott Will & Emery LLP

(57) ABSTRACT

Disclosed is an integrated circuit comprising an electrode arrangement for detecting the presence of a liquid, said electrode arrangement comprising a first electrode and a second electrode, wherein, prior to exposure of the electrode arrangement to said liquid, a surface of at least one of the first electrode and second electrode is at least partially covered by a compound that is soluble in the liquid; the electrical properties of the electrode arrangement being dependent on the amount of the compound covering said surface. An package and electronic device comprising such an IC and a method of manufacturing such an IC are also disclosed.

14 Claims, 3 Drawing Sheets

(56) References Cited

U.S. PATENT DOCUMENTS

Figure 1:
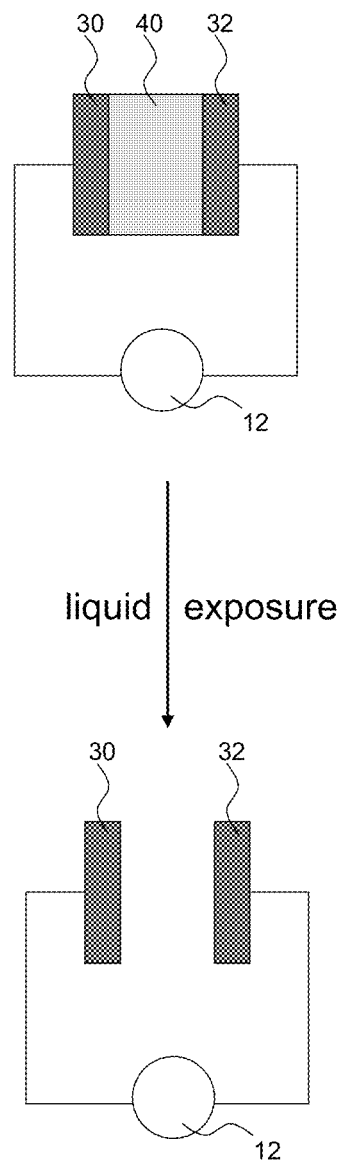

| | | | |
|---|---|---|---|
| 3,916,674 A * | 11/1975 | Miller et al. | 73/61.51 |
| 4,057,823 A | 11/1977 | Burkhardt et al. | |
| 4,565,455 A * | 1/1986 | Bloore et al. | 374/164 |
| 4,696,796 A * | 9/1987 | Oka et al. | 422/88 |
| 5,072,190 A * | 12/1991 | Martin | 324/663 |
| 5,110,441 A * | 5/1992 | Kinlen et al. | 204/418 |
| 5,557,263 A * | 9/1996 | Fisher et al. | 340/605 |
| 5,959,535 A * | 9/1999 | Remsburg | 340/604 |
| 6,073,480 A * | 6/2000 | Gokhfeld | 73/29.02 |
| 7,193,290 B2 * | 3/2007 | Benzel et al. | 257/467 |
| 8,779,548 B2 | 7/2014 | Ponomarev et al. | |
| 2008/0061323 A1 | 3/2008 | Yazawa et al. | |
| 2008/0191716 A1 | 8/2008 | Chen et al. | |

OTHER PUBLICATIONS

Morgan, Solubility Rules! Accessed Aug. 26, 2014.*
Solubility, accessed Aug. 25, 2014.*
Aero 07 Design for Corrosion Control, Boeing pp. 1-9.*
Galvonic Corrosion, Nick Gromiko, pp. 1-4.*
Extended European Search Report for Patent Appln. No. 09178227.6 (Jun. 11, 2010).
Communication pursuant to Article 94(3) EPC for counterpart application 09178227.6 (May 21, 2014).

* cited by examiner

INTEGRATED CIRCUIT AND MANUFACTURING METHOD THEREFOR

This application claims the priority under 35 U.S.C. §119 of European patent application no. 09178227.6, filed on Dec. 7, 2009, the contents of which are incorporated by reference herein.

BACKGROUND OF THE INVENTION

Nowadays, integrated circuits (ICs) routinely comprise patterned metallization layers for interconnecting circuit elements, e.g. transistor terminals in the substrate or to provide external access, e.g. bond pads, to the circuit elements that are embedded in the semiconductor device. Typically, the metallization layers are formed by stacking and patterning dielectric layers and metal layers to obtain the required interconnections. The dielectric and metal layers themselves may contain sub-layers. The dielectric layers typically comprise vias to conductively connect metal portions in the different metal layers with each other.

Rigorous testing of the ICs, e.g. when they are still part of a wafer, takes place to ensure that the IC operates correctly, e.g. is free of manufacturing defects. This is important because the IC may be integrated into an electronic device, where the failure of the IC in the electronic device would most likely cause the electronic device to exhibit faulty behavior. For this reason, significant efforts are made to ensure that defective ICs are removed from a batch of manufactured ICs to avoid field returns of electronic devices containing such ICs as much as possible. Field returns inconvenience the customer, and can lead to a loss of business because of the customer losing faith in the product. Nevertheless, it is very difficult to capture all defective ICs such that it cannot be avoided that some defective ICs enter the market, e.g. inside an electronic device. On the other hand, a returned faulty electronic device may have entered the market functioning correctly, where it is possible that the fault has developed through misuse of the semiconductor device, e.g. by the customer accidentally submerging the device in water. Obviously, in such a case, the manufacturer cannot be held responsible for the failure of the device.

It is difficult to establish why a semiconductor device returned from the field has failed. Re-engineering the device to determine the cause of failure is not always successful and is cost-prohibitive for single devices. U.S. Pat. No. 4,057,823 discloses a structure for a relative humidity monitor which can be built into an integrated circuit chip. A small area on a silicon chip is made porous by anodic etching. This region is then oxidized and a metal counter electrode is deposited over part of the porous area. Due to the relatively large surface area in the dielectric under the counter electrode and the openness of the structure, ambient moisture can quickly diffuse into the dielectric under the electrode and adsorb onto the silicon dioxide surface, such that changes in ambient humidity will be reflected by measurable changes in capacitance or conductance of the device.

A drawback of such a moisture sensor is that in other to determine if an electronic device returned from the field has been subjected to excess moisture, the sensor must be continuously monitored during the operational life of the electronic device and its measurements, or at least measurements exceeding a predefined threshold, stored for future read-out. This is an impractical solution, which furthermore cannot be used in passive components.

SUMMARY OF THE INVENTION

The present invention seeks to provide an IC in which its exposure to water does not have to be detected during the actual exposure.

The present invention further seeks to provide a method of manufacturing such an IC.

In accordance with a first aspect of the present invention, there is provided an integrated circuit comprising an electrode arrangement for detecting the presence of a liquid, said electrode arrangement comprising a first electrode and a second electrode, wherein, prior to exposure of the electrode arrangement to said liquid, a surface of at least one of the first electrode and second electrode is at least partially covered by a compound that is soluble in the liquid; the electrical properties of the electrode arrangement being dependent on the amount of the compound covering said surface.

This has the advantage that upon exposure of the electrode arrangement to the liquid of interest, the electrical properties, e.g. impedance of the electrode arrangement is permanently altered by at least part of the compound being dissolved, such that the read-out of the electrode arrangement is not time-critical to detect the exposure of the IC to the liquid. Consequently, a more reliable detection of such exposure is provided, which is particularly suitable in ICs that cannot be constantly or immediately read out to detect such exposure.

The detection of exposure of the IC to the liquid can simply be done by comparison of the actual electrical properties of the electrode arrangement with a reference value, which typically is measured at manufacture when the IC is known to operate correctly. In an embodiment, the IC may therefore further comprise a memory storing a known good value of said electrical properties such that the comparison may be made without having to return the IC to its origin of manufacture.

The IC may further comprise a measurement circuit conductively coupled to the electrode arrangement for measuring said electrical properties, which preferably is adapted to compare the measured value with the known good value stored in memory to determine if the IC has been exposed to the liquid. This for instance facilitates a retailer of the IC to verify if a returned faulty IC has been maltreated, i.e. exposed to the liquid, without requiring the IC to be sent to its origin of manufacture to make this determination.

Although preferable, it is not necessary for the measurement circuit to be integrated on the IC. Alternatively, the IC may further comprise a plurality of terminals conductively coupled to the first electrode and the second electrode respectively for measuring the impedance between said electrodes, such that the measurement may be performed off-chip.

In the IC of the present invention, the electrode arrangement may be modified with a compound that dissolves in any liquid of interest, e.g. any polar or any non-polar solvent. Most commonly, the liquid will be water, in which case the compound may be selected from the group comprising water-soluble sugars and salts, as these compounds are readily available and are known to influence the electrical properties of the electrode arrangement. However, it should be understood that any compound soluble in the liquid of interest may be used, as long as it affects the electrical properties of the electrode arrangement as previously described.

In an embodiment, the integrated circuit further comprises a substrate including a plurality of circuit elements and a metallization stack covering said substrate for providing interconnections between the circuit elements, wherein a metallization layer of said stack comprises at least one of the first electrode and the second electrode, said compound covering the at least one electrode region of said metallization layer.

In this embodiment, the electrode arrangement is integrated in the metallization stack, which means that the electrode arrangement can be provided using readily available process steps, most notably CMOS process steps, thus not adding to the complexity and cost of the IC manufacturing process. The aforementioned measurement circuit may be realized by some of the circuit elements.

In an embodiment, the first electrode may be comprised in the top metallization layer and the second electrode may be comprised in an underlying metallization layer, wherein the first electrode is perforated, and wherein the compound is further disposed between the first electrode and the second electrode. The presence of a perforated electrode has the advantage that the liquid can more easily access the compound to be dissolved.

The IC of the present invention may subsequently be packed, thereby providing a package that comprises an opening for enabling exposure of the compound to said liquid. Such a package may subsequently be integrated into an electronic device, in particular into portable electronic devices that are at risk of being exposed to a liquid upon misuse of the device, e.g. mobile communications devices, laptops, personal digital assistants and so on.

In accordance with another aspect of the present invention, there is provided a method of manufacturing an integrated circuit, comprising forming an electrode arrangement for detecting the presence of a liquid, said electrode arrangement comprising a first electrode and a second electrode; and covering a surface of at least one of the first electrode and second electrode with a compound that is soluble in the liquid; the electrical properties of the electrode arrangement being dependent on the amount of the compound covering said surface. Such a method provides an IC for which the impedance of the electrode arrangement is permanently altered by at least part of the compound being dissolved, such that the read-out of the electrode arrangement is not time-critical to detect the exposure of the IC to the liquid, as previously explained.

In an embodiment, the method further comprises providing a substrate; forming a plurality of circuit elements on said substrate; forming a metallization stack covering said substrate for providing interconnections between the circuit elements, and forming at least one of the first electrode and the second electrode in a metallization layer of said stack or on top of said metallization stack. This is particularly advantageous as the electrode arrangement forming the liquid immersion sensor can be integrated into a standard manufacturing process such as a CMOS process without requiring additional processing steps other than the deposition of the compound.

The compound may be deposited in any suitable manner, for instance by depositing a solution comprising the compound dissolved in a solvent over said surface; and subsequently evaporating the solvent, thus providing the compound covering at least one of the electrode surfaces at marginal additional cost.

In an embodiment, the step of forming at least one of the first electrode and the second electrode in a metallization layer of said stack comprises forming the second electrode in a further metallization layer underneath the metallization layer; forming the first electrode in top metallization layer, said first electrode comprising a plurality of perforations; etching a cavity between the first electrode and the second electrode; and filling said cavity with the compound. This yields an IC in which the liquid has improved access to the compound through said perforations.

BRIEF DESCRIPTION OF THE EMBODIMENTS

Figure 2:
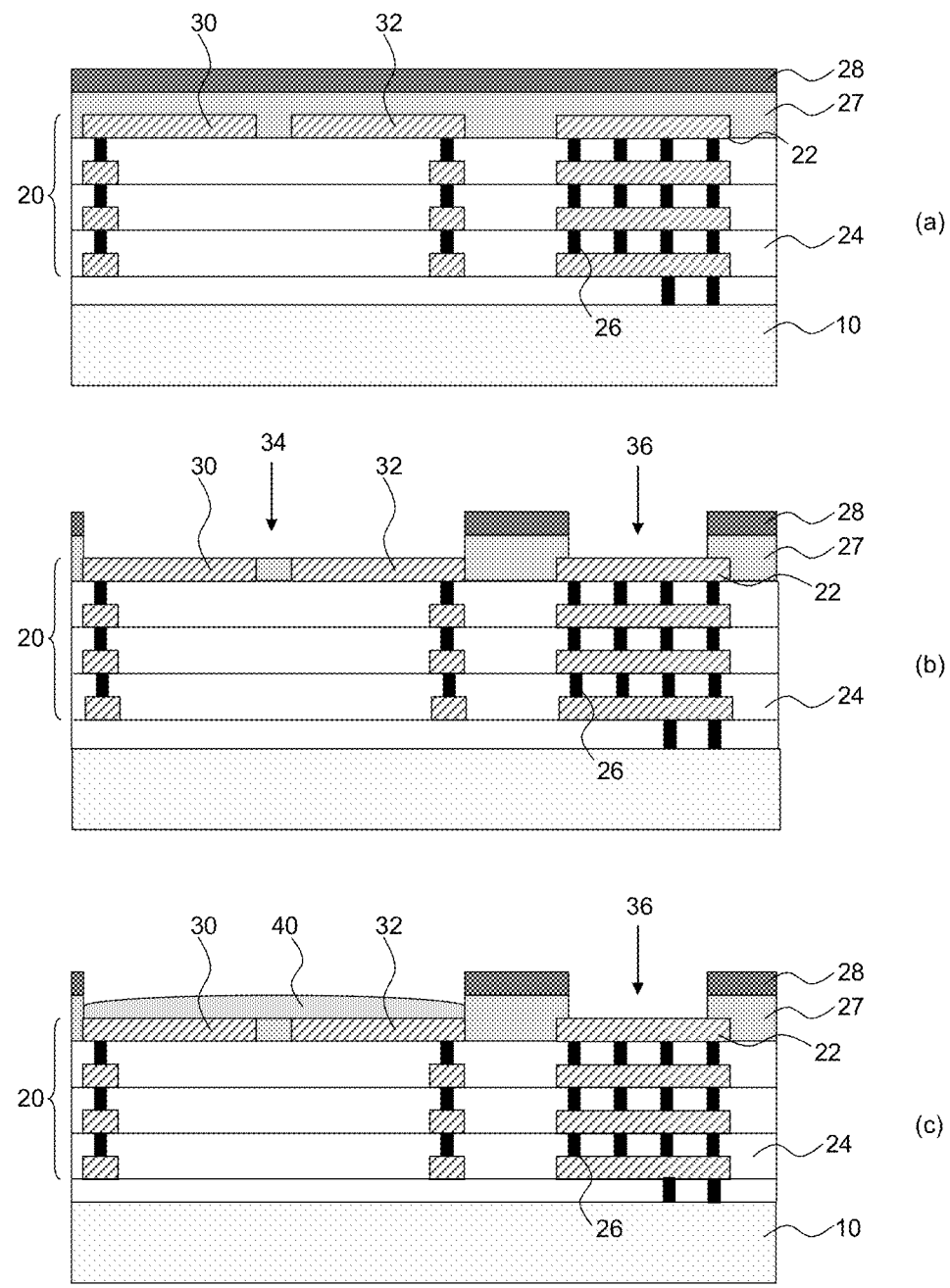
Figure 3:
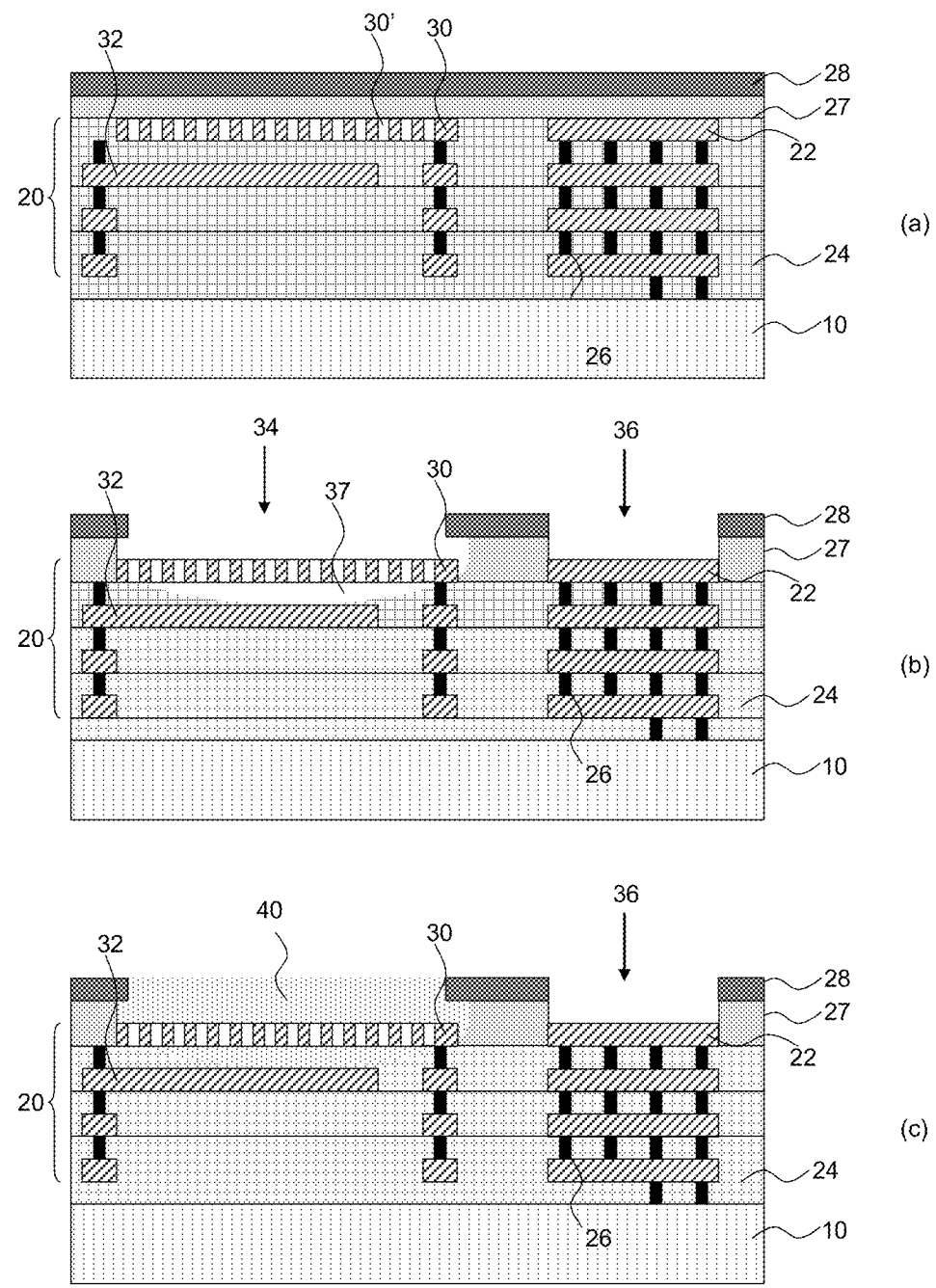

Embodiments of the invention are described in more detail and by way of non-limiting examples with reference to the accompanying drawings, wherein FIG. 1 schematically depicts the general concept of the present invention;

FIG. 2 schematically depicts an embodiment of a method of manufacturing an IC of the present invention; and FIG. 3 schematically depicts another embodiment of a method of manufacturing an IC of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

FIG. 1 schematically depicts the general principle of an IC in accordance with an embodiment of the present invention. The IC comprises an electrode arrangement including a first electrode 30 and a second electrode 32, at least one of which has a surface covered by a compound 40 that is soluble in a liquid of interest. In FIG. 1, the electrode arrangement comprises a capacitor in which the plates are formed by the first electrode 30 and the second electrode 32, with the compound 40 forming the dielectric between the plates. It will be understood that this particular arrangement has been shown by way of non-limiting example only. The skilled person will realize that many other arrangements are equally suitable, such as an arrangement in which the first electrode 30 has a surface coated with the compound 40, with the second electrode 32 forming a counter or reference electrode.

The invention is based on the insight that upon the compound 40 at least partially dissolving in the liquid of interest, as shown in FIG. 1, the impedance of the electrode arrangement is altered due to the change in dielectric constant and/or resistance caused by the at least partial removal of the compound 40 being dissolved in the liquid of interest.

A measurement circuit 12, which may be integrated on the IC or provided off-chip for connection to terminals that are conductively coupled to the respective first electrode 30 and the second electrode 32, is arranged to measure the electrical properties of the electrode arrangement, e.g. the impedance, at any given time to determine if the compound 40 has at least been partially removed, thus indicating the exposure of the IC to the liquid of interest. Such a measurement circuit 12 may be implemented in any suitable manner. Since it is well-known per se to measure electrical properties such as capacitance and impedance, the measurement circuit 12 will not be explained in further detail for reasons of brevity.

The exposure of the electrode arrangement to the liquid of interest is typically determined by comparison of the measured value of the electrical property with a reference value that has been determined at the manufacturing stage of the IC, at which stage the IC was known to operate in accordance with its specifications. For this reason, such a reference value is sometimes referred to as a known good value.

In an embodiment, this reference value is stored in a memory (not shown) on the IC. This memory may be implemented in any suitable manner. The measurement circuit 12 may be conductively coupled to the memory to enable the measurement circuit 12 retrieve the reference value during a measurement of the electrical properties of the electrode arrangement for comparison purposes as previously explained. The memory may be integrated in the measurement circuit 12.

The compound 40 may be soluble in more than one liquid. Depending on the application domain of the IC of the present invention, a compound 40 may be selected that is soluble in polar solvents, in non-polar solvents and so on. In many consumer electronics applications, the liquid of interest is water, as the electrode arrangement is used as a liquid immersion sensor to detect the exposure, e.g. immersion of the electronic device comprising the IC of the present invention to water as such exposure typically invalidates the warranty of the electronic device.

Any suitable compound 40 may be chosen. As there are numerous compounds 40 that are suitable for application in the electrode arrangement of the IC of the present invention, it is unfeasible to provide an exhaustive list of suitable compounds 40. However, it is noted that in case of the liquid of interest comprising water, non-limiting examples of suitable compounds 40 include water-soluble sugars, e.g. fructose, glucose, dextrose and so on, as well as water-soluble salts, e.g. NaCl, KCl, and so on.

An important advantage of the IC of the present invention is that the electrical properties of the liquid immersion sensor formed by the electrode arrangement comprising the first electrode 30 and the second electrode 32 as well as the liquid-soluble compound 40 are permanently changed upon exposure of the sensor to the liquid, as at least part of the compound 40 will be removed, i.e. dissolved, by the exposure to the liquid. This means that the sensor may be read out at any suitable time following the suspected exposure to the liquid. This makes the sensor suitable for use in passive devices e.g. passive RFID tags, where the measurement circuit 12 can only be powered when the IC is brought into a suitable RF field. Obviously, the present invention is equally suitable for use in active devices, e.g. devices permanently connected to a power source.

The IC of the present invention may be provided using any suitable manufacturing technology, such as CMOS, silicon-on-insulator and SiGe technologies. The IC comprises a substrate 10, e.g. a Si substrate, a SiGe substrate and so on, which typically comprises a plurality of circuit elements such as transistors, diodes, and so on, combinations of which from circuits. These may be analog or digital circuits. It should be understood that the present invention is not limited to specific types of ICs. The present invention may be included in any suitable IC, including digital ICs, analog ICs and mixed signal ICs. However, in an embodiment, the electrode arrangement is realized in the metallization stack of such an IC, as this has the advantage that little modification of a standard manufacturing process is required, thus facilitating the manufacture of an IC of the present invention at little additional cost.

An exemplary embodiment of the realization of the liquid immersion sensor of the present invention in such a metallization stack is shown in FIG. 2. As shown in step (a), the interconnections between the circuit elements in the substrate 10 to define the circuits are typically provided by a metallization stack 20, which by way of non limiting example may comprise a plurality of patterned metal layers 22 separated by dielectric layers 24. In FIG. 2, such a stacked connection is shown on the right hand side of the substrate 10.

Any suitable number of metal layers 12 and dielectric layers 14 may be present. Metal portions in different metal layers 22 may be conductively interconnected by one or more vias 26 formed in a dielectric layer 24 in between the respective portions of the metal layers 22. Any suitable material may be used to form the metallization stack 20, such as Ti, TiN, Al, Cu and combinations thereof to define the metal layers 22 and silicon oxide, silicon nitride, low-k dielectrics and other dielectric materials as well as combinations thereof to form the dielectric layers 24. Although in FIG. 1 these layers are depicted as single layers, it should be understood that these layers themselves may comprise a stack of layers, as is common manufacturing practice in contemporary semiconductor technologies such as sub-micron CMOS technologies. For instance, the metal layers 22 may comprise Ti, TiN, AlCu, TiN stacks, whereas the dielectric layers 24 may be stacks of e.g. FSG (fluorine-doped silica glass), $SiO_2$ and HDPOX (high-density plasma oxide).

In accordance with the present invention, the top metal layer 22 of the metallization stack 20 comprises the first electrode 30 and the second electrode 32, which may be formed in the top metal layer 22 or may be deposited on top of the top metal layer 22. Both embodiments are equally feasible. Any suitable metal may be used for the first electrode 30 and the second electrode 32. Preferably, the metal used is the same metal as used in the metallization stack 20 such that the electrodes may be realized using the same processing steps used for the formation of the metal layers 22 such that the complexity of the IC manufacturing process is not significantly increased, i.e. the manufacturing cost of the IC is not significantly increased. Since it is well-known to the skilled person how to form such electrodes, this will not be further explained for reasons of brevity only.

The metallization stack 20 is typically protected from external influences such as humidity and scratching by several passivation or scratch protection layers, here depicted by two layers 27 and 28 by way of non-limiting example only. Any suitable material may be used for such layers, e.g. an oxide layer 27 and a nitride layer 28. More than two layers may be used.

In step (b), the protective layers, i.e. layers 27 and 28 in FIG. 2, are patterned to form a first access region 34 to the electrode arrangement including the first electrode 30 and the second electrode 32 and a second access region 36 to the aforementioned stacked connection. Such regions may be formed in any suitable manner, e.g. by deposition of a mask layer (not shown), patterning the mask layer and subsequently subjecting the exposed regions of the protective layers to a suitable etchant, e.g. dry (plasma) etch or a wet etch.

Subsequently, as shown in step (c), the access region 34 is immersed with a solution comprising the compound 40, after which the solvent is removed, e.g. through evaporation to leave a layer, e.g. crust, of the compound 40 on the first electrode 30 and the second electrode 32.

At this point, it is noted that although not explicitly shown in FIG. 2, the IC obviously may comprise additional circuitry, e.g. the measurement circuit 12 and further functional circuitry.

It is not necessary that both the first electrode 30 and the second electrode 32 are formed in or on the top metallization layer 22 of the metallization stack 20. FIG. 3(a) shows an alternative embodiment in which the first electrode 30 is formed in the top metallization layer 22, and the second electrode 32 is formed in the metallization layer underneath the top metallization layer 22. The first electrode 30 comprises perforations 30'.

Such perforations may be formed by adjusting the lithography mask that is used to pattern the electrode. Instead of a blank/uniform metal area the electrode, a lithography mask defining small holes may be used. Consequently, when processing the metal layer defining the electrode, small portions of the electrode are left uncovered by the deposited resist and thus etched away, thereby forming the perforations. This allows for the formation of such a perforated electrode without requiring additional processing steps.

Next, as also explained in the context of step (b) in FIG. 2, the access regions 34 and 36 may be formed, e.g. by etching. This is shown in step (b). Due to the presence of the perforations 30' in the top electrode 30, the etchant also penetrates the upper dielectric layer 24 through the perforations 30', thus forming a cavity 37 in between the first electrode 30 and the second electrode 32. The second electrode 32 acts as an etch-stop in this etching step.

Variations to the above sequence will be apparent to the skilled person. For instance, a dry etch may first be used to open the passivation stack, followed by a vapor HF etch to remove the dielectric between both electrodes. The HF etch is highly anisotropic, which aids the opening of the space underneath and between the perforation holes.

In step (c), the compound 40 is deposited in the access region 34 in dissolved form, with this solution also filling the cavity 37 through the perforations 30', after which the solvent is removed e.g. through evaporation, thus leaving a layer, e.g. crust, of the compound 40 covering both the first electrode 30 and the second electrode 32. Preferably, a saturated solution of the compound 40 is used to ensure that removal of the solvent can be achieved as quickly as possible, as well as to ensure that the cavity 37 is filled as much as possible by the compound 40.

For the sake of completeness, it is pointed out that it is not necessary that at least one of the electrodes of the liquid immersion sensor is located in the top metal layer of the metallization stack. Both electrodes may be located in the lower metal layers.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated circuit comprising:
an electrode arrangement configured to detect presence of a liquid, said electrode arrangement comprising a first electrode and a second electrode, wherein, prior to exposure of the electrode arrangement to said liquid, a surface of at least one of the first electrode and second electrode is at least partially covered by a compound that is soluble in the liquid, wherein the electrical properties of the electrode arrangement are dependent on the amount of the compound covering said surface; and
a substrate including a plurality of circuit elements and a metallization stack covering said substrate for providing interconnections between the circuit elements, wherein a metallization layer of said stack comprises at least one of the first electrode and the second electrode, said compound covering the at least one electrode region of said metallization layer, and wherein the electrical properties of the electrode arrangement are permanently changed by exposure to the liquid.

2. The integrated circuit of claim 1, further comprising:
a memory that is configured to store a known good value of said electrical properties.

3. The integrated circuit of claim 1, further comprising:
a measurement circuit conductively coupled to the electrode arrangement that is configured to measure said electrical properties.

4. The integrated circuit of claim 1, further comprising:
a plurality of terminals conductively coupled to the first electrode and the second electrode respectively that are configured to measure the impedance between said electrodes.

5. The integrated circuit of claim 1, wherein the liquid is water.

6. The integrated circuit of claim 5, wherein the compound is selected from a group comprising water-soluble sugars and salts.

7. The integrated circuit of claim 1, wherein the first electrode is comprised in said top metallization layer and the second electrode is comprised in an underlying metallization layer, the first electrode is perforated, and the compound is further disposed between the first electrode and the second electrode.

8. A package comprising the integrated circuit of claim 1, said package comprising an opening for enabling exposure of the compound to said liquid.

9. An electronic device comprising the package of claim 8.

10. A method of manufacturing an integrated circuit, comprising:
forming an electrode arrangement for detecting the presence of a liquid, said electrode arrangement comprising a first electrode and a second electrode;
covering a surface of at least one of the first electrode and second electrode with a compound that is soluble in the liquid, wherein electrical properties of the electrode arrangement are dependent on an amount of the compound covering said surface;
providing a substrate;
forming a plurality of circuit elements on said substrate;
forming a metallization stack covering said substrate for providing interconnections between the circuit elements;
forming at least one of the first electrode and the second electrode in a metallization layer of said stack or on top of said metallization stack; and
permanently changing the electrical properties of the electrode arrangement by exposure to the liquid.

11. The method of claim 10, wherein the step of forming at least one of the first electrode and the second electrode in the metallization layer of said stack further comprises:
forming the second electrode in a further metallization layer underneath the metallization layer;

forming the first electrode in the metallization layer, wherein said first electrode comprising a plurality of perforations;
etching a cavity between the first electrode and the second electrode; and
filling said cavity with the compound.

12. The method of claim 10, wherein the step of covering the surface of at least one of the first electrode and the second electrode with the compound that is soluble in the liquid further comprises:
depositing a solution comprising the compound dissolved in a solvent over said surface; and subsequently evaporating the solvent.

13. The integrated circuit of claim 1, wherein at least part of the compound is dissolved by exposure to the liquid.

14. The method of claim 10, further comprising dissolving at least part of the compound by exposure to the liquid.

* * * * *